United States Patent
Monty

(10) Patent No.: US 10,624,715 B2
(45) Date of Patent: *Apr. 21, 2020

(54) DENTAL LASER SYSTEM AND TREATMENT METHOD

(75) Inventor: Nathan Paul Monty, Charlton, MA (US)

(73) Assignee: Convergent Dental, Inc., Needham, MA (US)

(*) Notice: Subject to any disclaimer, the term of this patent is extended or adjusted under 35 U.S.C. 154(b) by 1032 days.

This patent is subject to a terminal disclaimer.

(21) Appl. No.: 13/019,706

(22) Filed: Feb. 2, 2011

(65) Prior Publication Data

US 2011/0189628 A1    Aug. 4, 2011

Related U.S. Application Data

(63) Continuation-in-part of application No. 12/847,739, filed on Jul. 30, 2010, now Pat. No. 8,251,984.

(60) Provisional application No. 61/229,997, filed on Jul. 30, 2009.

(51) Int. Cl.

| | |
|---|---|
| A61C 1/00 | (2006.01) |
| H01S 3/223 | (2006.01) |
| H01S 3/03 | (2006.01) |
| H01S 3/097 | (2006.01) |
| A61B 18/20 | (2006.01) |

(52) U.S. Cl.
CPC .............. *A61C 1/0046* (2013.01); *H01S 3/03* (2013.01); *H01S 3/09702* (2013.01); *H01S 3/2232* (2013.01); *A61B 18/20* (2013.01); *H01S 3/0315* (2013.01)

(58) Field of Classification Search
CPC ....... A61C 1/0046; A61B 18/20; H01S 3/036; H01S 3/223

USPC ............................................... 606/2, 3, 9–14
See application file for complete search history.

(56) References Cited

U.S. PATENT DOCUMENTS

| | | | |
|---|---|---|---|
| 5,388,987 A | 2/1995 | Badoz et al. | |
| 5,596,593 A * | 1/1997 | Crothall | H01S 3/0975 372/82 |
| 6,156,030 A * | 12/2000 | Neev | 606/10 |
| 6,402,739 B1 * | 6/2002 | Neev | 606/9 |
| 6,482,199 B1 | 11/2002 | Neev | |
| 6,603,792 B1 * | 8/2003 | Chomsky | H01S 3/08081 372/55 |
| 2003/0078499 A1 * | 4/2003 | Eppstein | 600/439 |
| 2003/0100824 A1 | 5/2003 | Warren et al. | |

(Continued)

FOREIGN PATENT DOCUMENTS

| | | |
|---|---|---|
| DE | 102009005194 A1 | 7/2010 |
| EP | 0437955 A1 | 7/1991 |

(Continued)

OTHER PUBLICATIONS

Martin Werner "Ablation of hard biological tissue and osteotomy with pulsed CO2 lasers", Nov. 2006, Heinrich Heine University, pp. 1-167.*

(Continued)

*Primary Examiner* — Boniface N Nganga
(74) *Attorney, Agent, or Firm* — Goodwin Procter LLP

(57) ABSTRACT

An improved dental laser system has been developed to cut enamel quickly and precisely, without detrimental residual energy, to provide a replacement for conventional high speed rotary burrs and commercially available dental laser systems.

22 Claims, 8 Drawing Sheets

(56) References Cited

U.S. PATENT DOCUMENTS

| | | | |
|---|---|---|---|
| 2004/0114130 A1* | 6/2004 | Nguyen | G01N 1/24 356/36 |
| 2005/0259942 A1* | 11/2005 | Temelkuran | A61B 18/201 385/147 |
| 2006/0189965 A1 | 8/2006 | Litvak et al. | |
| 2006/0195072 A1* | 8/2006 | Miller | 606/2 |
| 2007/0041418 A1* | 2/2007 | Laughman et al. | 372/55 |
| 2007/0195839 A1* | 8/2007 | Monty | H01S 3/0315 372/38.05 |
| 2008/0172047 A1* | 7/2008 | Altshuler et al. | 606/9 |
| 2010/0082019 A1* | 4/2010 | Neev | 606/9 |

FOREIGN PATENT DOCUMENTS

| | | |
|---|---|---|
| WO | WO-97/10768 A2 | 3/1997 |
| WO | WO-2007/038975 A1 | 4/2007 |
| WO | WO-2009/052866 A1 | 4/2009 |
| WO | WO-2010/083825 A1 | 7/2010 |
| WO | WO-2011/014802 A2 | 2/2011 |

OTHER PUBLICATIONS

Zhang et al., "OPtimization of Line Cuts Strategy for Bone Tissue Ablation Using Short-Pulsed Co2 Laser Based on Thermal Relaxation", Nov. 18-19, 2010, CURAC Annual Meeting, vol. 1475 pp. 1-7.*

Stopp et al., "A new concept for navigated laser surgery", Jul. 2007, Laser Med Sci vol. 23: pp. 261-266.*

Ivanenko, "Wet bone ablation with mechanically Q-switched high-repetition-rate CO2 laser", Applied Physics, B 67, 395-397, Jul. 6, 1998 (Year: 1998).*

International Search Report for PCT/US2011/023483 dated Jan. 13, 2012 (6 pages).

Shlomo Assa, et al. Ablation of dental hard tissues with a microsecond pulsed carbon dioxide laser operating a 9.3 [mu]m with an integrated scanner, Proceedings of SPIE, vol. 6843, Feb. 7, 2008 (Feb. 7, 2008), pp. 684308-684308-7, XP055193947.

Ertl, et al., "Hard Tissue Ablation With Pulsed CO2 Lasers", SPIE vol. 1800 pp. 176-181 (.

Gerold K.H. Eyrich, "Laser-osteotomy induced changes in bone", Medical Laser Application 20 (2005) 25-36.

M. Frentzen, et al., "Osteotomy with 80μs CO2 laser pulses—histological results", Lasers Med Sci (2003)18:119-124.

Werner, et al., "CO2 laser free-form processing of hard tissue", Therapeutic Laser Applications and Laser-Tissue Interactions III, Feb. 24, 2010 vol. 6632 663202-1-663202-6.

Ivanenko, et al., Ablation of hard bone tissue with puled CO2 Lasers, Medical Laser Application 20 (2005) 13-23.

G. D. Rajitha Gunaratne, Riaz Khan, Daniel Fick, Brett Robertson, Narendra Dahotre & Charlie Ironside (2016): A review of the physiological and histological effects of laser osteotomy, Journal of Medical Engineering & Technology, DOI: 10.1080/03091902.2016. 1199743 (published online Jun. 27, 2016).

Ivanenko, et al., "Hard tissue ablation with subμs CO2 laser pulses with the use of air-water spray", Optical Biopsy and Tissue Optics, Proceedings of SPIE vol. 4161 (2000).

Ivanenko, et al., "In Vivo animal trials with a scanning CO2 laser Osteotome," Lasers in Surgery and Medicine 37:144-148 (2005).

Ivanenko, et al., "System development and clinical studies with a scanning CO2 laser osteotome," Optical Interactions with Tissue and Cells XVII, Proc. of SPIE vol. 6084, 60840H, (2006) 1605-7422.

Kahrs, et al., "Planning and simulation of microsugrical laser bone ablation," Int J CARS (2010) 5:155-162 (DOI 10.1007/s11548-009-0303-4).

Kuttenberger, et al., "Bone healing of the sheep tibia shaft after carbon dioxide laser osteotomy; histological results," Lasers Med Sci (2010) 25:239-249 (DOI 10.1007/s10103-009-0714-z).

Nair, et al., "Observations on pulpal response to carbon dioxide laser drilling of dentine in healthy human third molars," Lasers in Medical Science (2005) 19: 240-247 (DOI 10.1007/s10103-004-0317-7).

Werner, et al., "CO2 laser "milling" of hard tissue" Optical Interactions with Tissue and Cells XVIII, Proc. of SPIE vol. 6435, 64350E, (2007) 1605-7422.

Zhang, et al., "Optimization of Line Cut Strategy for Bone tissue ablation using Short-pulsed CO2 laser based on thermal relaxation,".

Kuttenberger, et al., "Computer-Guided CO2-laser osteotomy of the SheepTibia: Technical prerequisites and first resultes," Photomedicine and Laser Surgery, vol. 26, No. 2, 2008, pp. 129-136 (DOI: 10.1089/pho.2007.2139).

\* cited by examiner

| FEATURE | MIN. VALUE | NOMINAL VALUE | MAX. VALUE | (UNITS) |
|---|---|---|---|---|
| WAVELENGTH | 9 | 9.25 - 9.4 | 10 | µm |
| PULSE LENGTH | 0.1 | 20 | 30 | µsec |
| PULSE ENERGY | 0.1 | 11 | 30 | mJ |
| FLUENCE AT FOCUS | 0.14 | 7.94 | 50 | $J/cm^2$ |
| PULSE REPETITION RATE | 0.10 | 0.5 to 2 | 4 | kHz |
| LASER BEAM SPOT SIZE DIAMETER | 300 | 420 | 2000 | µm |
| LASER BEAM SPOT SIZE DIAMETER | 0.03 | 0.042 | 0.2 | cm |
| HARD TISSUE REMOVAL RATE | 0.1 | 0.15 | 0.5 | g/sec |
| VOLUMETRIC REMOVAL RATE | 0.03 | 0.05 | 0.17 | $cm^3/sec$ |
| TREATMENT TIME | 0 | 20 | 180 | secs |
| LASER BEAM ANGLE OF INCIDENCE | 0 | 90 | 90 | degrees |
| FLUIDIC FLOW ANGLE OF INCIDENCE | 0 | 65 | 90 | degrees |
| DUTY CYCLE | 0.01 | 4-9 | 20 | percent |

FIG. 3

| PULSE LENGTH (μseconds) | | | | |
|---|---|---|---|---|
| | 5 | 10 | 15 | 20 |
| 250 (Hz) | | | | |
| LASER POWER (WATTS) | 1.1/1.05 | 2.1/1.9 | 3.1/3.0 | 4.2/3.9 |
| PULSE ENERGY (mJ) | 4.2 | 7.6 | 12.0 | 15.6 |
| FLUENCE (j/cm$^2$) | 5.3 | 9.6 | 15.2 | 19.8 |
| 500 (Hz) | | | | |
| LASER POWER (WATTS) | 2.1/2.05 | 4.1/3.8 | 6.1/5.7 | 7.8/7.8 |
| PULSE ENERGY (mJ) | 4.1 | 7.6 | 11.4 | 15.6 |
| FLUENCE (j/cm$^2$) | 5.2 | 9.6 | 14.4 | 19.8 |
| 1000 (Hz) | | | | |
| LASER POWER (WATTS) | 4.0/3.9 | 7.3/7.3 | 11.1/10.4 | 14.4/14.8 |
| PULSE ENERGY (mJ) | 3.9 | 7.3 | 10.4 | 14.8 |
| FLUENCE (j/cm$^2$) | 4.9 | 9.2 | 13.2 | 18.8 |
| 1500 (Hz) | | | | |
| LASER POWER (WATTS) | 6.1/5.6 | 11.2/10.8 | 16.7/14.3 | 21.5/20.0 |
| PULSE ENERGY (mJ) | 3.7 | 7.2 | 9.5 | 13.3 |
| FLUENCE (j/cm$^2$) | 4.7 | 9.1 | 12.0 | 16.8 |

FIG. 5

| SAMPLE NUMBER | | | | | |
|---|---|---|---|---|---|
| | 1 | 2 | 3 | 4 | 5 |
| REMOVED (grams) | 0.26 | .024 | .029 | 0.32 | 0.40 |

DENTAL LASER SYSTEM AND TREATMENT METHOD

CROSS-REFERENCES TO RELATED APPLICATIONS

This application is a continuation-in-part of and claims priority under 35 U.S.C. § 120 to co-pending, commonly owned U.S. patent application Ser. No. 12/847,739, entitled DENTAL LASER SYSTEM USING MIDRANGE GAS PRESSURE, filed Jul. 30, 2010, which claims priority to and the benefit of U.S. provisional patent application Ser. No. 61/229,997, filed Jul. 30, 2009. The entire disclosures of these two applications are hereby incorporated herein by reference in their entireties.

FIELD OF INVENTION

The present invention relates to systems and methods for removing decay, cutting, drilling or shaping hard tissue, removing and cutting soft tissue, modifying hard tissue for caries inhibition and modifying hard tissue surface conditions to aid in adhesion to hard tissue. The present invention applies to oral tissue, gums and teeth, e.g., to human or animal oral tissue, gums and teeth, and other biological materials.

BACKGROUND OF THE INVENTION

A tooth has three layers. The outermost layer is the enamel which is the hardest and forms a protective layer for the rest of the tooth. The middle and bulk of the tooth is made up of the dentin, and the innermost layer is the pulp. The enamel and dentin are similar in composition and are roughly 85% mineral, carbonated hydroxyapatite, while the pulp contains vessels and nerves which are sensitive to pressure and temperature. In this application of drilling or contouring or conditioning the enamel and dentin, the pulp's temperature sensitivity is of concern. A rise in temperature of 5.5° Celsius can lead to permanent damage of the tooth's pulp.

Over the last 10 to 15 years, research has taken place to define laser parameters that allow the enamel and dentin of a tooth to be removed, drilled, contoured or conditioned, all being removal processes, without heating the pulp. Ideally the laser pulses should vaporize the enamel and dentin converting the mass to gas with minimal residual energy remaining in the dentin to heat the pulp.

The use of lasers in dentistry has been considered since the introduction of the laser. Dental lasers used to drill and cut were the initial applications. High energy density pulses were initially used, but these pulses could potentially damage the tooth pulp or soft tissue, so lower energy pulse configurations were explored. With lower peak power energy pulses longer pulse times were used, which affected the tooth enamel detrimentally.

Various laser wavelength interactions were explored, UV to the Far Infrared, to understand the optical coupling efficiencies. Optical coupling was found to be critical with the greatest coupling being in the 2.7-3.0 μmeter and 9.3-9.6 μm wavelength ranges. When reflectance is considered, the 9.3-9.6 μmeter range was found to couple up to 3 times better than any other wavelength range.

Having identified the most effective coupling wavelength, the time and threshold to ablate hard tissue had to be determined. Research has shown that the thermal relaxation time of hard tissue is 1 to 2 μsec with a threshold ablation energy of approximately 5 mJ (milli-Joules).

Recognizing the need for laser pulses in the 9.3 to 9.6 μmeter wavelength range with microsecond pulse widths and pulse energies of 5 to 15 mJ, DC excited TEA (transversely excited atmospheric) lasers were adopted. Since the TEA lasers have a very short pulse length, i.e., hundreds of nanoseconds, the TEA lasers were modified for long pulse operation and modified pulse shapes. Additionally a RF (Radio Frequency) CW (continuous wave) laser was studied, but its shortest pulse length was only 50 μseconds, so the pulses heated the hard tissue significantly more than the shorter pulse widths.

To date, RF excited $CO_2$ CW lasers seeking the greatest RF to Optical efficiency typically operate at 70 to 100 Torr (or about 9,332-13,332 Pascals (Pa)) and the shortest pulse lengths produced are typically 50 μseconds. Typical gas pressure for a normal RF excited $CO_2$ laser, used in the prior art, is 80 Torr (or about 10,665 Pa). $CO_2$ TEA lasers operating at atmospheric pressure produce 9.3 to 9.6 μmeter pulses at hundreds of nanoseconds in pulse length. TEA lasers generally do not operate in sealed operation, do not have long operating lifetimes or high pulse repetition rates, and are expensive to package. While a "long pulse" TEA laser can be manufactured to produce the optimal $CO_2$ laser pulsing parameters, TEA lasers are larger and more expensive than RF excited lasers and therefore are not an ideal match for a dental laser application—where size and cost are critical. None of the approaches to date, therefore, have produced a full set of optimal parameters in a commercially acceptable format for effectively working with enamel and dentin, without heating the pulp.

SUMMARY OF THE INVENTION

In accordance with one aspect a method for treating hard tissue is provided, the method including generating a laser beam with a repetition rate greater than about 0.5 kHz, directing the laser beam at an exposed surface of the hard tissue (e.g., tooth enamel, dentin, etc.), and removing at least a portion of the exposed surface of the hard tissue without substantially increasing temperature of adjacent tissue (e.g., tooth pulp). The laser beam may have one or more of: a wavelength in a range of about 9 μm to about 10 μm, a pulse length in a range of up to about 30 μsec, a fluence up to about 50 $J/cm^2$, a repetition rate up to about 4 kHz, and a nominal diameter of up to about 2000 μm. In some embodiments, the laser beam of the method for treating hard tissue includes laser pulses such that a pulse energy associated with each pulse is in a range of up to about 30 mJ.

In some embodiments, the laser beam of the method for treating hard tissue is generated by a $CO_2$ laser. The $CO_2$ laser may operate with a gas in a range of about 260 Torr to about 600 Torr, and the gas may be $^{12}C(^{18}O)_2$ gas or $^{12}C(^{16}O)_2$ gas.

In some embodiments, the laser beam is directed at the exposed surface of the hard tissue utilizing a hollow waveguide. The positioning of the hollow waveguide relative to the exposed surface of the hard tissue may be controlled manually or robotically. The laser beam may be moved relative to the exposed surface of the hard tissue to remove incrementally the portion of the exposed surface of the hard tissue. In some embodiments, a remaining portion of the hard tissue does not exhibit any substantial charring. The hard tissue is removed at a rate of up to about 0.5 g/sec, or at a volumetric rate of up to about 1.7 $cm^3$/sec. The hard tissue may be removed by explosive vaporization.

In some embodiments, the method for treating hard tissue includes directing a fluidic flow at the exposed surface of the hard tissue. The fluidic flow may be selected from the group consisting of a fluid, a gas, and combinations thereof. The fluidic flow may be adapted to contribute to either controlling temperature of the hard tissue, or reducing redeposition of removed material onto the exposed surface of the hard tissue, or both. The fluidic flow may be directed to the exposed surface of the hard tissue at an angle of incidence in a range from about zero degrees to about 90 degrees. The hard tissue treated by the method may be dental enamel, dentin, bone, or combination thereof.

In some embodiments, the exposed surface of the hard tissue at which the laser beam is directed during a single pulse has a cross-sectional area of up to about 0.03 cm$^2$. In some embodiments, directing the laser beam includes delivering a sequences of pulses for up to about three minutes. The laser beam may be directed to the exposed surface of the hard tissue at an angle of incidence up to about 90 degrees. Directing the laser beam may include focusing the laser beam using a lens having a focal length, and positioning the exposed surface of the hard tissue relative to the lens at a distance slightly less than the focal length. In some embodiments, directing the laser beam includes modifying the laser beam using an optical system, such that a profile of the modified laser beam is non Gaussian.

In accordance with another aspect, a system for treating hard tissue is provided, the system including a laser beam generator for generating a laser beam with a repetition rate greater than about 0.5 kHz. The system also includes an optical component for directing the laser beam at an exposed surface of the hard tissue, and a laser beam controller for controlling at least one laser beam parameter, such that at least a portion of the exposed surface of the hard tissue is removed without substantially increasing a temperature of adjacent tissue.

The laser beam parameters may be one or more of: a wavelength in a range of about 9 μm to about 10 μm, a pulse length in a range of up to about 30 μsec, a fluence up to about 50 J/cm$^2$, a repetition rate up to about 4 kHz, a nominal diameter of up to about 2000 μm, and a pulse energy in a range of up to about 30 mJ.

The laser beam generator of the system for treating hard tissue may be a $CO_2$ laser beam generator. The $CO_2$ laser beam generator may operate with a gas in a range of about 260 Torr to about 600 Torr, and the gas may be $^{12}C(^{18}O)_2$ gas or $^{12}C(^{16}O)_2$ gas.

In some embodiments, the optical component of the system for treating hard tissue includes a hollow waveguide. The system for treating hard tissue may include a handpiece for manually positioning the hollow waveguide relative to the exposed surface of the hard tissue. In some embodiments, the system includes a robotic controller for positioning the hollow waveguide relative to the exposed surface of the hard tissue. The robotic controller may be configured to move the laser beam relative to the exposed surface of the hard tissue to remove incrementally the portion of the exposed surface of the hard tissue.

In some embodiments, the hard tissue is removed at a rate of up to about 0.5 g/sec, or at a volumetric rate of up to about 0.17 cm$^3$/sec. The hard tissue may be removed by explosive vaporization. A remaining portion of the hard tissue may not exhibit any substantial charring.

In some embodiments, the system for treating hard tissue includes a fluid dispenser for directing a fluidic flow at the exposed surface of the hard tissue. The fluidic flow dispensed by the fluid dispenser may be a fluid, a gas, or combinations thereof. The fluidic flow may be adapted to contribute to either controlling temperature of the hard tissue, or reducing redeposition of removed material onto the exposed surface of the hard tissue, or both. The fluid dispenser may direct the fluidic flow to the exposed surface of the hard tissue at an angle of incidence in a range from about zero degrees to about 90 degrees. The hard tissue may be dental enamel, dentin, bone, or combination thereof.

In some embodiments, the laser beam controller of the system for treating hard tissue configures the laser beam as a sequences of pulses for up to about three minutes. The exposed surface of the hard tissue at which the laser beam may be directed during a single pulse may have a cross-sectional area of up to about 0.03 cm$^2$.

In some embodiments, the optical component is configured to direct the laser beam to the exposed surface of the hard tissue at an angle of incidence up to about 90 degrees. The optical component may include a lens having a focal length for focusing the laser beam, such that the exposed surface of the hard tissue relative to the lens is at a distance slightly less than the focal length. In some embodiments, the optical component modifies the laser beam, such that a profile of the modified laser beam is non Gaussian.

DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention. In the drawings:

FIG. 3 is a table of typical laser parameters and dental system performance parameters in accordance with the present invention.

FIG. 5 is a table of the laser parameters and performance parameters measured during the operation of an experimental laser system in accordance with the present invention.

DETAILED DESCRIPTION

Figure 1:
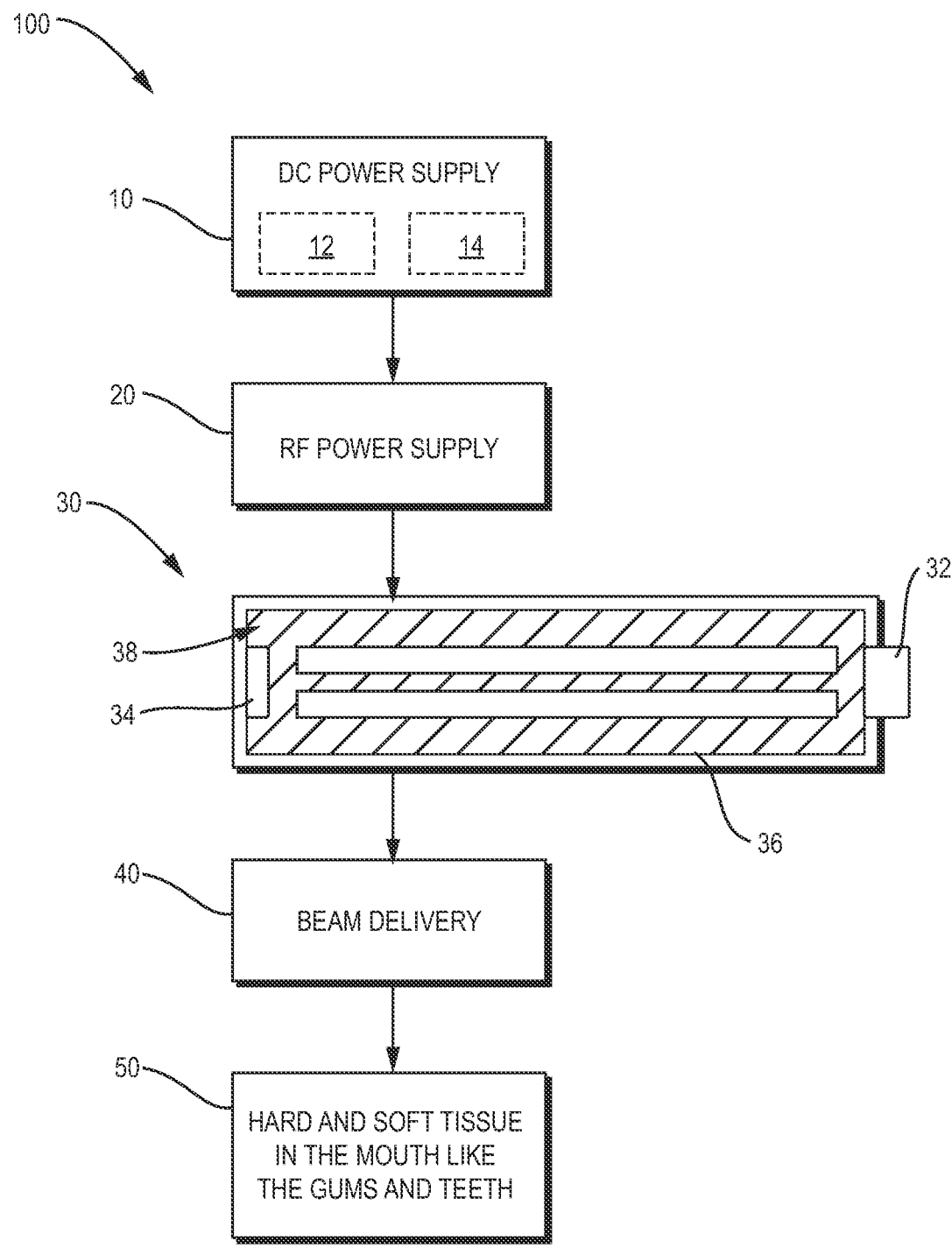
FIG. 1 is a block diagram of an embodiment of a dental laser system, in accordance with aspects of the present invention.

Hereinafter, aspects of the present invention will be described by explaining illustrative embodiments in accordance therewith, with reference to the attached drawings. While describing these embodiments, detailed descriptions of well-known items, functions, or configurations are typically omitted for conciseness.

It will be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

With respect to dental laser systems, the wavelength with the highest absorption in hydroxyapatite has been determined to be in the 9.3 to 9.6 μmeter range and the thermal relaxation time of hydroxyapatite to be a maximum of 2 μseconds at the 9.3 to 9.6 μm wavelength range. Therefore, the ideal pulse parameters for removing the hydroxyapatite appear to be 9.3 to 9.6 μmeter energy in a less than 50 μsecond format. In accordance with one preferred embodiment, a laser is provided that produces a beam having pulse parameters for removing hydroxyapatite using 9.3 to 9.6 μm wavelength energy in a less than 50 μsecond format.

The 9.3 to 9.6 μm energy is typically produced using a $CO_2$ laser with a laser gas mixture of $^{12}C(^{18}O)_2$, wavelength selective resonator optics, more expensive inter-cavity wavelength devices, or a combination of the three. In accordance with the present invention, the 50 μsecond pulses are produced with a fast pulse rise and fall time, which is effected by laser gas pressure. In order to produce pulses of less than or equal to 50 μseconds in length, gas pressure of at least about 260 Torr (or about 34,663 Pa) is used.

According to one preferred embodiment, a $CO_2$ gas laser, in either a waveguide or slab resonator format, filled with gas that is in a range of about 260 Torr to about 600 Torr (or about 34,700-80,000 Pa), is RF excited for use in all dental applications. A range of about 260 to about 600 Torr (or about 34,700-80,000 Pa) may be preferable in many dental applications. Since waveguide and slab resonators are generally known in the art, they are not discussed in detail herein.

In some embodiments, the pressure can be in a range of about 280-550 Torr (or about 37,330-73,327 Pa), or about 300-500 Torr (or about 39,996-66,661 Pa), about 320-450 Torr (or about 42,663-59,995 Pa), about 340-400 Torr (or about 45,329-53,328 Pa), as examples.

The laser can be operated in CW or pulsed mode for cutting and drilling applications, respectively. DC and RF power supplies are configured to aid in low power CW operation, while supporting high peak power pulse operation. The laser output is coupled to a beam delivery system to deliver the optical energy to the patient. The laser provides the 9.3 to 9.6 nm energy wavelength, with a fast pulse rise and fall time (e.g., not more than about 50 μseconds, and typically not more than 20 μsecond), sealed off operation, high repetition rates in a small reliable package.

FIG. 1 shows an embodiment of a dental laser system 100 according to aspects of the present invention. In the embodiment of FIG. 1, a DC power supply 10 is provided that rectifies as AC input power (not shown). In one preferred embodiment, the DC power supply 10 is comprised of a continuous wave (CW) DC section 12 and a pulsed DC section 14. The DC section 12 is sized to run the laser for CW applications, such as soft tissue cutting, and the peak power DC section 14 supplies the peak energy for pulsing applications, such as hard tissue or bone modification.

Item 20 is a radio frequency (RF) power supply for the conversion of the DC energy to RF energy in the 40 to 125 MHz range. Item 30 is a $CO_2$ laser with the RF energy as an input and 9.3 to 9.6 μmeter optical energy as an output, via an output coupler 32. And item 40 is a beam delivery apparatus, which delivers the optical energy from the laser to item 50, which represents a patient's mouth.

$CO_2$ laser 30 in this embodiment includes a rear mirror 34 and a laser discharge area 36. The mirror 34 directs optical energy through the laser discharge area 36. The output coupler 32 couples the beam out of the laser. In this case the laser is a gas laser, so the output coupler couples the beam out of the laser without allowing the laser gas out. The $CO_2$ laser 30 also includes a laser gas pressure vessel 38 that is filled with a gas at a pressure in a range of about 260 to about 600 Torr (or about 34,700-80,000 Pa).

The output laser energy is provided to the beam delivery apparatus 40, where it can then be directed to a target, such as a patient's mouth. In this embodiment, the beam delivery apparatus 40 can include flat or curved mirrors or a combination configured to steer optical energy output from the $CO_2$ laser.

In this exemplary configuration, the dental laser system 100 can operate at both low power CW operation, e.g., <10 watts, for the cutting of gums and oral tissue, and high peak power pulsing operation, e.g., >5 mJ pulse energy at 1 to 50 μseconds pulse widths up to 10 kHz. The $CO_2$ laser 30 can operate at wavelengths between 9 and 11 μm. The laser system 100 preferably provides high peak power pulsing operation at the ideal absorption wavelength for the hydroxyapatite in dental hard tissues. The pulse widths and pulse energy are ideally suited to ablate hydroxyapatite, leaving very little residual heat in the tooth to damage the pulp even up to 10 kHz in operation.

Figure 2:
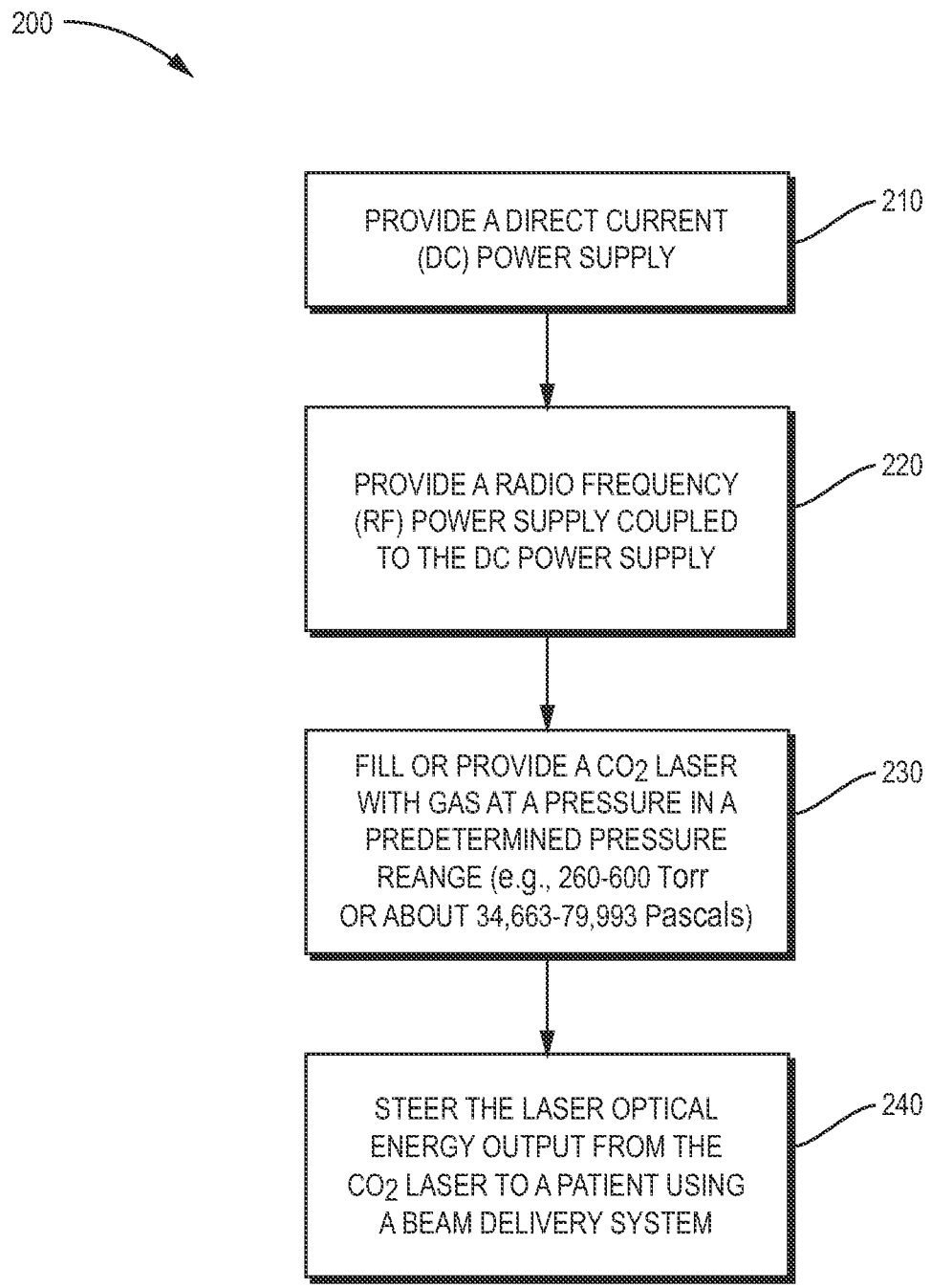
FIG. 2 is a flowchart of an embodiment of outputting laser optical energy from a $CO_2$ dental laser system, in accordance with aspects of the present invention.

FIG. 2 is an embodiment of a method of outputting laser optical energy from a $CO_2$ dental laser system. The method 200 includes providing a direct current (DC) power supply in step 210, providing a radio frequency (RF) power supply coupled to the DC power supply in step 220, filling a $CO_2$ laser with gas at a pressure in a predetermined pressure range (e.g., about 260 to about 600 Torr (or about 34,700-80,000 Pa)) in step 230, and steering the laser optical energy output from the from the $CO_2$ laser to a patient using a beam delivery system 240.

FIG. 3 is a table listing a number of typical laser operational parameters and associated dental system performance parameters discussed in more detail, below. Values are provided for minimum and maximum conditions, as well as nominal conditions contemplated for use with various embodiments and in various applications of the invention. It should be noted that the minimum and maximum values are not boundaries and that actual values may be lower or higher by 10% or 20% or more of the total range for each parameter.

More specifically, a hard tissue, such as tooth enamel and dentin, comprises water and minerals. While extensive dental laser studies have been conducted at hard tissue's water and mineral absorption bands, the research emphasis has been on the efficiency of absorption. Dental practices are primarily concerned with cutting speed and resolution. Building on the efficiency results from prior research, an exemplary dental laser system was built with the flexibility to change pulse width and average power levels at hard tissue's mineral absorption band to improve cutting efficacy, as described in detail below in the Example.

Figure 4:
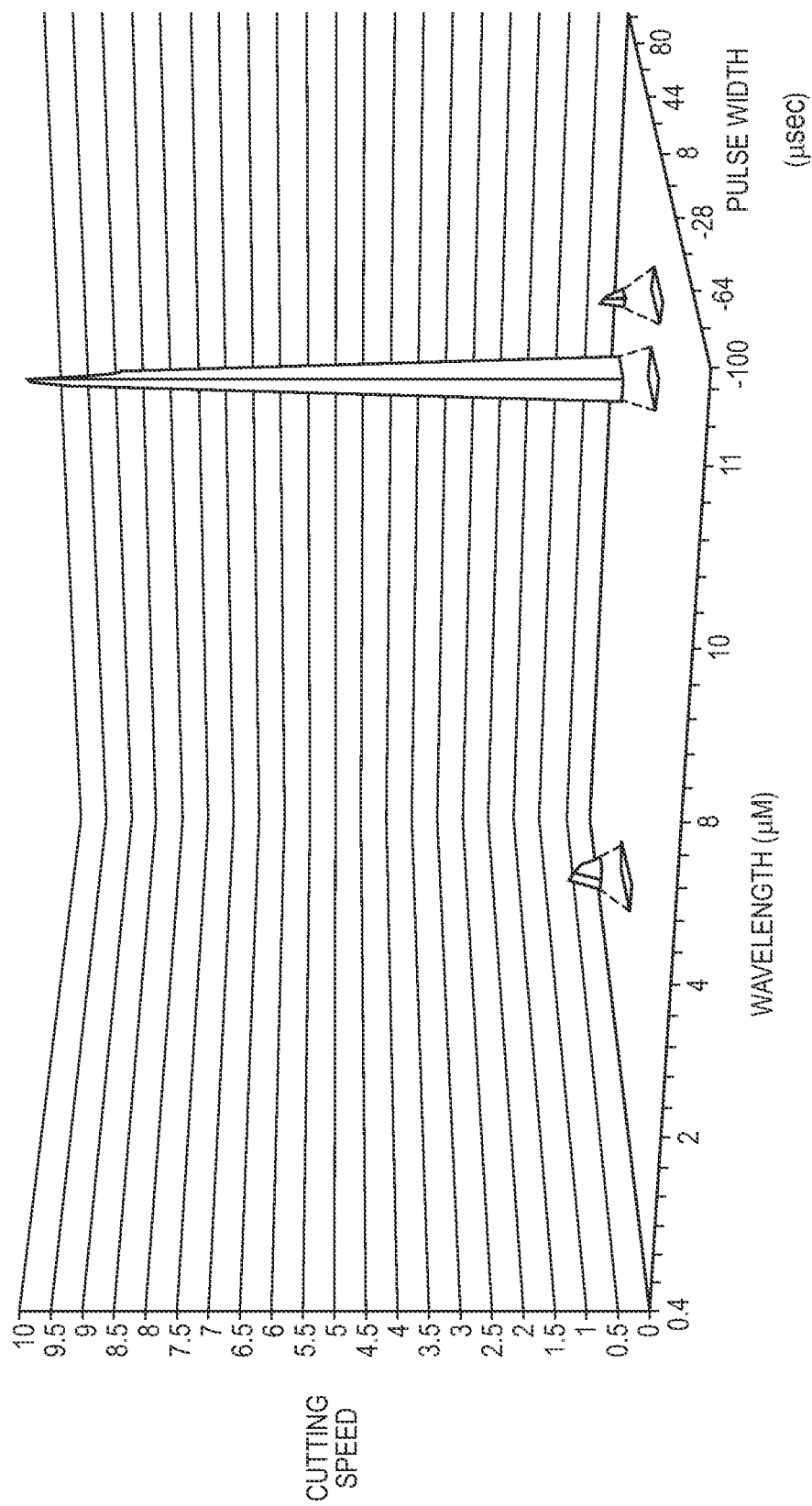
FIG. 4 depicts absorption of radiation by tooth enamel at various wavelengths and pulse widths.

Cutting or drilling hard tissue in a tooth primarily equates to removing the tissue's hardest outer layer, the enamel. Enamel is a biological composite generally containing by volume approximately 12% water, approximately 85% mineral (carbonated hydroxyapatite), and about 3% protein and lipids. Accordingly high efficacy may be achieved by cutting or drilling the 85% mineral constituent of the enamel. It has been shown that dental enamel's mineral content has a peak absorption (8000 $cm^{-1}$) at 9.6 μm, absorbing electromagnetic radiation up to ten times higher than at 10.6 μm or other laser wavelengths in the visible or other IR region. In the exemplary system described in the Example, a 9.4 μm laser was used as the "proof of concept" because at present it is a commercially available laser having a wavelength close to 9.6 μm. FIG. 4 shows that the difference in absorption at 9.4 μm and 9.6 μm is not significant.

It is desirable that the laser parameters for dental hard tissue ablation, namely pulse duration and laser wavelength, be selected such that practical ablation rates can be achieved while minimizing the residual energy, ER, deposition in the tooth. Residual energy can be the energy directed by a laser beam to the hard tissue (e.g., tooth enamel) that does not cause tissue ablation, but instead, is absorbed into the surrounding tissue. In general, the absorption of radiation in enamel is heterogeneous due to the inherent microstructure of the enamel. As a result, the mechanism of ablation varies with the nature of the primary absorber in which the laser radiation is absorbed. For example, absorption in water results in water mediated ablation and absorption in the bulk of the enamel rods leads to melting and explosive vaporization. As described above, the absorption at 9.6 μm occurs in the enamel rod mineral content typically causing explosive vaporization, as explained below. Because the tooth enamel includes approximately 85% mineral, ablation efficiency of enamel is usually high at or near the mineral absorption wavelength of 9.6 μm.

Due to the strong wavelength absorption of $CO_2$ laser radiation, the laser energy is usually deposited in a very thin absorption layer at the surface of the hard tissue (e.g., tooth enamel). This can result in a strong internal pressure build-up in a small volume of the hard tissue. If the pressure rise time is shorter than the thermal relaxation time of the tissue (e.g., the time during which the heat generated in the hard tissue is dissipated), the pressure finally exceeds the ultimate tensile strength of the tissue causing the tissue to tear apart in a localized micro-explosion, also called explosive vaporization. The excess heat is ejected together with heated ablation debris and is thus removed from the tissue. Accordingly, in explosive vaporization, thermal damage to the surrounding tissue can be prevented. $CO_2$ lasers may be suitable for explosive vaporization, because their wavelength is strongly absorbed in the mineral component (hydroxyapatite) of bone tissue, such that a small tissue volume can be heated extremely quickly.

As described above, explosive vaporization may occur when the pressure rise time is shorter than the thermal relaxation time of the tissue. Due to the nature of explosive vaporization, the incident laser energy is either consumed and ejected in the ablation process, or absorbed in the tissue in the form of heat, or residual energy ER. The residual energy can cause heating of the surrounding tissue (e.g., internal tissue of the tooth) as opposed to the removal of hard tissue. Therefore, minimizing the ER can increase ablation efficiency.

A desired pulse duration or pulse length can be on the order of the relaxation time for axial heat conduction ($\tau z$) of the deposited energy in the tissue surface. For laser pulse durations substantially longer than $\tau z$, the laser energy may be conducted away from the enamel surface into the interior pulp of the tooth during the laser pulse, resulting in inefficient surface heating. If the pulse duration is too short, however, the required power density to cause explosive vaporization may be too high, likely causing the generation of a plasma in the plume of ablated material that shields the surface and reduces the efficiency of ablation.

The thermal relaxation time of the deposited laser energy in enamel at the wavelength of approximately 9.6 μm is about 1 μsec. Therefore ablation efficiency of hard tissue using a radiation wavelength at or near the mineral absorption wavelength of 9.6 μm, may be increased using pulses approximately 1 μsec in duration. In one experiment the lowest residual energy was noted at 9.6 μm wavelength, using 5 μsec pulse length and 15 $J/cm^2$ fluence (described below) where less than 25% of the incident energy was absorbed as residual energy.

Though pulses of short duration can increase the ablation efficiency by decreasing the amount of residual energy absorbed, the longer the pulse length the lower the cost per watt of average laser power. Therefore, it is beneficial to select a pulse length that can simultaneously decrease the amount of residual energy absorbed and the cost per watt of the laser power. Accordingly, it is important to understand the residual energy, ER, as a function of pulse length. The shorter laser pulses, e.g., 5-20 μsecs, ablate at a significantly lower ablation threshold and leave a lower residual energy than the longer laser pulses that can achieve higher ablation rates per pulse. Pulse lengths of less than or equal to 20 μsecs with fluences of 10 $J/cm^2$ or greater lead to low residual energy and high cutting efficiency. Longer pulse lengths, e.g., longer than 20 μsec, may lead to higher ablation rates per pulse, but higher residual energy and lower ablation efficiency. Shorter pulse lengths, e.g., 5 to 20 μsec in duration, may have higher ablation efficiency and lower residual energy, but may result in lower ablation rates per pulse. Duty cycle (i.e., pulse length divided by total time between pulses can be varied as desired. See FIG. 3 for typical duty cycle values.

In addition to the absorption wavelength and the pulse length required for high ablation efficiency, the hard tissue enamel rod heating speed, leading to explosive vaporization, generally depends on pulse energy density, commonly referred to as fluence. In other words, the total energy delivered to a target site by one laser pulse may be expressed as the product of fluence and area of the treatment site. A threshold, i.e., minimal radiation exposure $\phi_{th}$ ($J/cm^2$) is theoretically necessary to induce an ablating micro-explosion at a treatment site by causing a sufficient pressure build-up. Taking into account the losses due to diffusion or reflection of radiation, however, the actual fluence required to be directed toward the enamel may be greater than the theoretical minimum. For example, to accumulate the necessary energy in the absorption layer of the hard tissue to reach the theoretical energy threshold, the energy may need to accumulate fast enough so as to compensate losses from thermal diffusion. Accordingly, there is a minimum required fluence threshold. For example, the ablation thresholds are about 0.5 and 3 J/cm$^2$ for 9.6 μm and 10.6 μm, respectively, after correction for reflectance losses. A desirable fluence is above the threshold for explosive vaporization, but one that minimizes the residual energy, ER, leading to high ablation efficiency. Considering the 1 μsec thermal relaxation time and the 0.5 J/cm$^2$ ablation threshold, a low residual energy in one embodiment occurs at 5 μsec pulse length and 15 J/cm$^2$ fluence. The ablation rate of enamel can saturate above 25 J/cm$^2$, and, hence a desired fluence is generally between about 1 and about 25 J/cm$^2$. Note, however, that higher fluences, up to about 50 J/cm$^2$ can be used. Fluences lower than 1 J/cm$^2$ can be used, for example, to pit the surface of the enamel to increase bonding of a cover layer or coating.

Generally, the speed of ablation of hard tissue depends on the average laser power used. Average laser power can be expressed as the product of power per pulse and the number of pulses, or power per pulse times the pulse repetition rate. Longer pulses, e.g. longer than 25 μsec in duration, can ablate more material per pulse, but shorter pulses, e.g., shorter than 20 μsec in duration, are more efficient at ablating dental hard tissue. Assuming similar average powers, ablation rates can be determined by the product of the ablation per pulse and the pulse repetition rate. Therefore shorter pulse lengths having lower residual energy levels can lead to higher dental cutting efficacy because more pulses per second, a higher repetition rate, can be utilized for the same average power. Without practical concerns, higher average powers lead to faster dental laser system ablation rates. But, higher laser average power may lead to a higher product cost, and the human hand limits scanning efficiency above repetition rates of about 1 to 2 kHz. Rates up to 4 kHz may be employed. Additionally, computer controlled robotic systems may be employed advantageously, to precisely control the application and location of the laser beam to the hard tissue, e.g., to cut a contour to receive a crown or pre-formed filling.

A 9.3 μm wavelength experimental dental system used pulse widths of 35 to 75 μsec with fluences of 1 to 6 J/cm$^2$, and repetition rates up to 400 Hertz. This dental laser system, with an integrated scanner, was effective in cutting dental hard tissue with substantially no temperature rise, but cut very slowly. The long pulse lengths and low fluence led to cutting speeds that are not desirable for general clinical use, and are not significantly better than the conventional drilling systems using rotary dental burrs.

Many known dental laser systems operate by exploding the water in hard tissue at wavelengths of 2.7 to 3.0 μm. Cutting hard tissue through water absorption is referred to as "thermo-mechanical" or "water-mediated" ablation. During rapid heating, the inertially confined water can create enormous substructure pressures that can lead to the explosive removal of the surrounding mineral matrix. Several studies of hard tissue ablation in the radiation wavelength λ at or near 3.0 μm indicate that large particles are ejected with high velocity, which strongly supports the mechanism of a water-mediated explosion process. One commercially available 2.78 μm wavelength dental laser system operates at relatively long pulse widths of 140 μsec, fluence of 32 to 60 J/cm$^2$, having a repetition rate of up to 50 Hertz. The relatively high pulse energy of this system requires a low repetition rate corresponding to an equivalent average power level. The longer pulse lengths, and associated higher pulse energies, also lead to higher residual energy, ER, in the tooth.

Example

An experimental dental laser system was constructed to operate at 9.4 μm wavelength with pulse widths of about 5 to 20 μsec, fluence of about 4 to 15 J/cm$^2$, and repetition rates of about 250 to 2000 Hertz. The parameters of this dental laser system, such as wavelength, pulse width, fluence, and repetition rate provide an average power level substantially similar to that of the commercial system, allowing for a comparison of the performance of the two systems.

Extracted human molar samples were used for ablation of enamel thereupon using this experimental system. The molars were stored in household bleach, and cleaned by hand with isopropyl alcohol. The molars were mounted on their sides, or by the root, in Plaster of Paris. Thermocouple holes were created with diamond tipped drills and saws using water soluble cutting fluid. Drilled molars were manually rinsed with tap water to remove the cutting fluid. Minimal preparation of the molars was deliberate to mimic dental office applications.

The molar samples were irradiated with a Coherent Diamond™ 225i slab laser excited with a RF power supply model # D64/84 RF Amp/LC Filter from Coherent in Bloomfield, Conn. The laser contains optical beam correction components so the beam quality is specified at a M2 of 1.3. The laser beam was directed through and modulated by an AO switch, model # AGM-4010AJ1MD with RF power supply model # E41277, both from IntraAction Corporation of Bellwood, Ill. The laser modulated pulses were delivered through an articulating arm model # PLATA1042 from Laser Mechanisms of Novi, Mich. The laser was focused to a spot size of 169 μm in diameter using a 78 mm FL plano/spherical lens. Some of the molars were mounted in Plaster of Paris on their sides so the cutting trials were performed on the relatively flat side of the molar eliminating the difference of geometry of various molar cusp regions.

The molars were hydrated during cutting by a CoolMist Portamist Model #60M12 using compressed air at 135 psi. The mist angle was approximately 45° to the cutting angle, the cut angle (i.e., the angle of incidence of the laser beam) being nearly 90° i.e., vertical or perpendicular to the cutting surface. It should be understood, however, that these angles are illustrative and cut angles other than 90° and mist angles other than 45° are also within the scope of the invention.

The laser pulse rise time was measured to be 75 μsec, so that all laser pulsing was initiated for 75 μsec. Then the AO Switch was triggered to create 5 to 20 μsec pulse widths with no rise or fall time. The average power of the 225i laser was checked at the factory by Coherent, and confirmed in the final configuration with both an Ophir model # FL-30OA-LP-SH and model # F-150A-SH-V1-ROHS connected to an Ophir Nova, serial #44797, optical power display meter. Pulse durations of 5, 10, 15, and 20 μsec were used with repetition rates of 250, 500, 1000, and 1500 Hertz for cutting the enamel of the molars. The laser and performance parameters of this system, as measured during the operation, are presented in a table in FIG. 5.

Some of the extracted human molars were mounted with their roots mounted in Plaster of Paris. Teeth were cut on the molar cusps where the geometry varies and the enamel thickness is the greatest. The molars were hydrated as described above. The laser optical and beam delivery arrangement described above was used, except a 20 μsec pulse length and a 2 kHz repetition rate was used.

Thermocouples were mounted at various locations in the molars to measure the rise in temperature at various locations in the interior of the molars. One thermocouple was mounted up through the root of the molar. Three other thermocouples were mounted below, at, and above the enamel line respectively. Prefabricated insulated thermocouples, type K Chromel-Alumel, 0.05" diameter cable, with a miniature K-Type connector were used for temperature measurement. The thermocouples were mounted in the drilled holes in good thermal contact and were held in place with thermally conductive epoxy, Resin Technology Group, Part # DP012209-1. The thermocouples voltages were converted to temperatures using a Fluke 80TK Thermocouple Module, model # FLU890TK mounted directly into a Fluke 77 Series digital voltmeter. The same optical arrangement as that described above was used, and 20 μsec pulse lengths at 2 kHz repetition rates were utilized, cutting continuously for three minutes.

Two additional molars were mounted by the root in Plaster of Paris and cut with the same optical system and hydrated as described above. A 20 μsec pulse length and 2 kHz repetition rate was used for the cutting of these two molars.

Figures 6, 7:
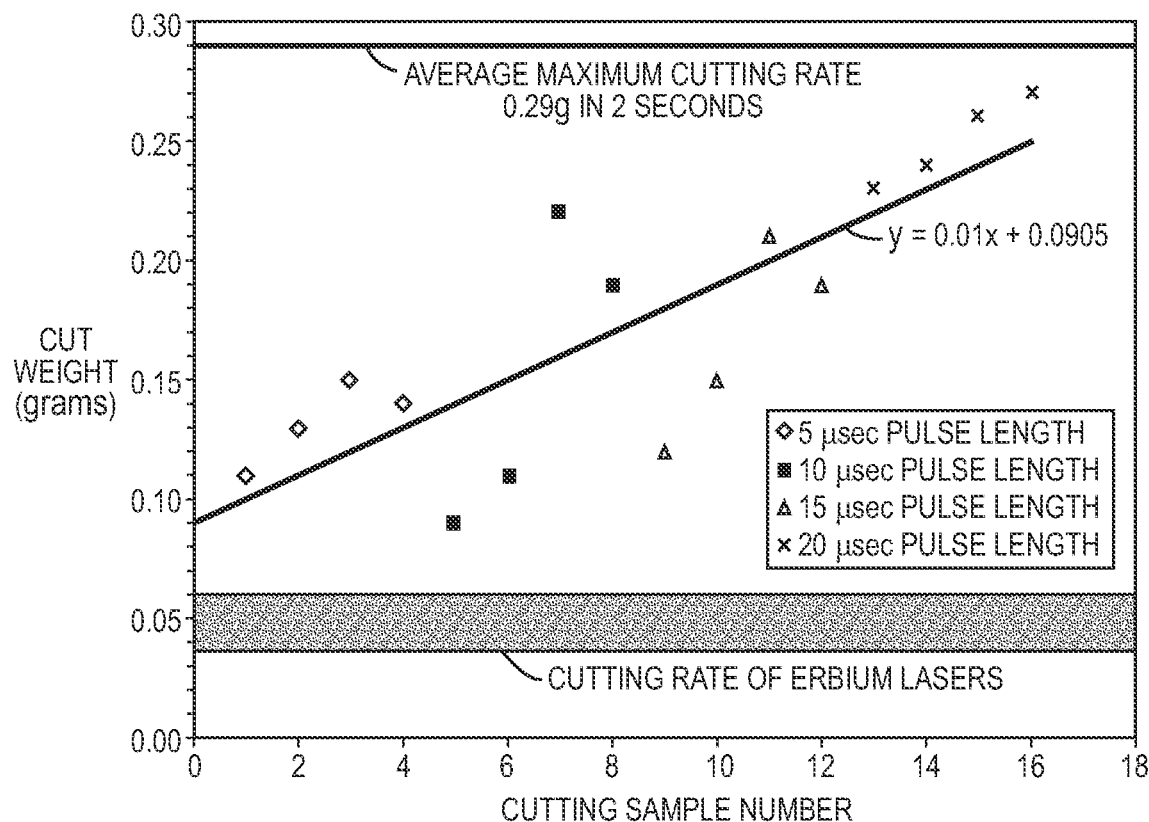
FIG. 6 depicts the rates of removal of tooth enamel by weight corresponding to treatment using laser beams having different parameters in accordance with the present invention.
FIG. 7 presents a table of the rates of removal of tooth enamel on different molars corresponding to one set of laser parameters in accordance with the present invention.

Sixteen molars were cut to measure the rate of removal of enamel by weight. FIG. 6 depicts the removal rate for the sixteen molars, where each molar is cut using a unique combination of pulse length and repetition rate (e.g., 5 μsec and 250 Hz, 5 μsec and 1.5 kHz, 15 μsec and 250 Hz, 15 μsec and 1 kHz, 20 μsec and 1.5 kHz, etc.). FIG. 6 also shows the average rate of cutting by weight using a conventional system, such as the Erbium dental laser. The projected achievable cutting rates, obtained by linear interpolation are also shown in FIG. 6.

In addition to the laser beam parameters (e.g., pulse length, repetition rate, pulse energy, fluence at focus, etc.) the variables that can impact the enamel cutting speed include flatness of the side of the molars, the elapsed time since a molar was extracted, and the steadiness of the hand-held laser system cutting tip. When a pulse repetition rate of about 1 kHz or greater is used, scanning of the targeted region of the hard tissue may be used. Substantially steadily directing a laser beam to the targeted region can impact the cutting speed. In general, however, this experimental system was about five times faster than the known systems including the Er:YAG and Er:YSGG systems that have volumetric removal rates of approximately 0.31 and 0.33 cm$^3$/min.

Five molars were cut to measure the rate of removal of enamel by volume. These molars were irradiated with a laser beam configured to delivers pulses of 20 μsec pulse length, 2 kHz repetition rate, 9.7 mJ pulse energy, and 21 J/cm$^2$ fluence at focus. The typical average density of enamel, e.g., carbonated hydroxyapatite, is 2.94 g/cm$^3$. The removal rates (by weight) are listed in the table presented in FIG. 7.

The spot size (i.e., area of the treatment region) and energy profile over the spot size are also important parameters. For example, even at a lower fluence, higher cutting rates were achieved at a spot size of about 250 μm in diameter, which may yield a fluence of about 10 J/cm$^2$ compared to a smaller spot size (e.g., 169 μm in diameter), yielding a fluence of about 20 J/cm$^2$. One of the reasons for the increased cutting speed at the lower fluence is the energy distribution across the spot size. When a plano/convex focus lens is used, the focused spot energy profile may be Gaussian i.e., a substantial amount of pulse energy is delivered at or near the focal point of the lens, which is usually an area near the center of the spot. A comparatively small amount of energy is delivered to the remaining area of the spot. In some instances, the energy delivered to the focal region of the spot can be above the ablation threshold while that delivered to the non-focal region may be below the ablation threshold. The energy in the "wings of the Gaussian energy pulse profile" (i.e., the energy directed to the non-focal regions) which is below the ablation energy can be absorbed as residual energy causing undesired heating of the tissue.

Thus, cutting when the enamel was positioned substantially at the focus can cause small craters below the cut surface. By positioning the enamel slightly above the focus, the amount of energy delivered at or near the focal region can be reduced, and, accordingly, less energy is consumed in ablating portions of the enamel below the cut surface. Correspondingly more pulse energy can be available for ablation in the non-focal region of the spot size, thereby achieving substantially uniform ablation in the target spot. Aspheric adaptive beam shaping optics may also be used to create a "flat top" or "top hat" energy distribution at focus, such that relatively less pulse energy is delivered near the focal region and relatively more energy may be delivered to the non-focal region of the spot, so that substantially all pulse energy is utilized for ablating the surface of the hard tissue. Alternatively or in addition, adaptive optics may be used to modify the optical pulse energy distribution to be non-Gaussian, substantially maintaining the energy in the entire spot above ablation threshold, thereby reducing the amount of residual energy consumed.

The performance of this system according to the present invention was compared with that of the commercial system. Charing occurred in the tooth when the commercial system was used. Even though this exemplary system cut tooth enamel at about five times faster than the commercial system, cutting using this exemplary system did not cause any substantial increase in temperature of adjacent tissue, and no charring. Moreover, due to the larger pulse lengths and larger pulse energy, the commercial system was less precise compared to the exemplary system. The larger pulse energies of the commercial system may also have affected the texture of the tooth. For example, at the bottom of a tooth cut using the commercial system, a section of enamel separated and lifted off the dentin. The separation may have been caused by the undesired heating of the enamel which thermally expands faster than the dentin and may mechanically separate therefrom. Accordingly, the instant invention provides higher removal rates coupled with more precise removal location, yielding a much more suitable dental treatment system than presently available.

In order to measure the heating of the internal tissue of the molars caused by this exemplary system, four molars were cut with thermocouples mounted therein as described above. In a first molar the thermocouple was located in the nerve chamber. In a second molar the thermocouple was located below the enamel line. In a third molar the thermocouple was located at the enamel line. In a fourth molar the thermocouple was located above the enamel.

Figure 8:
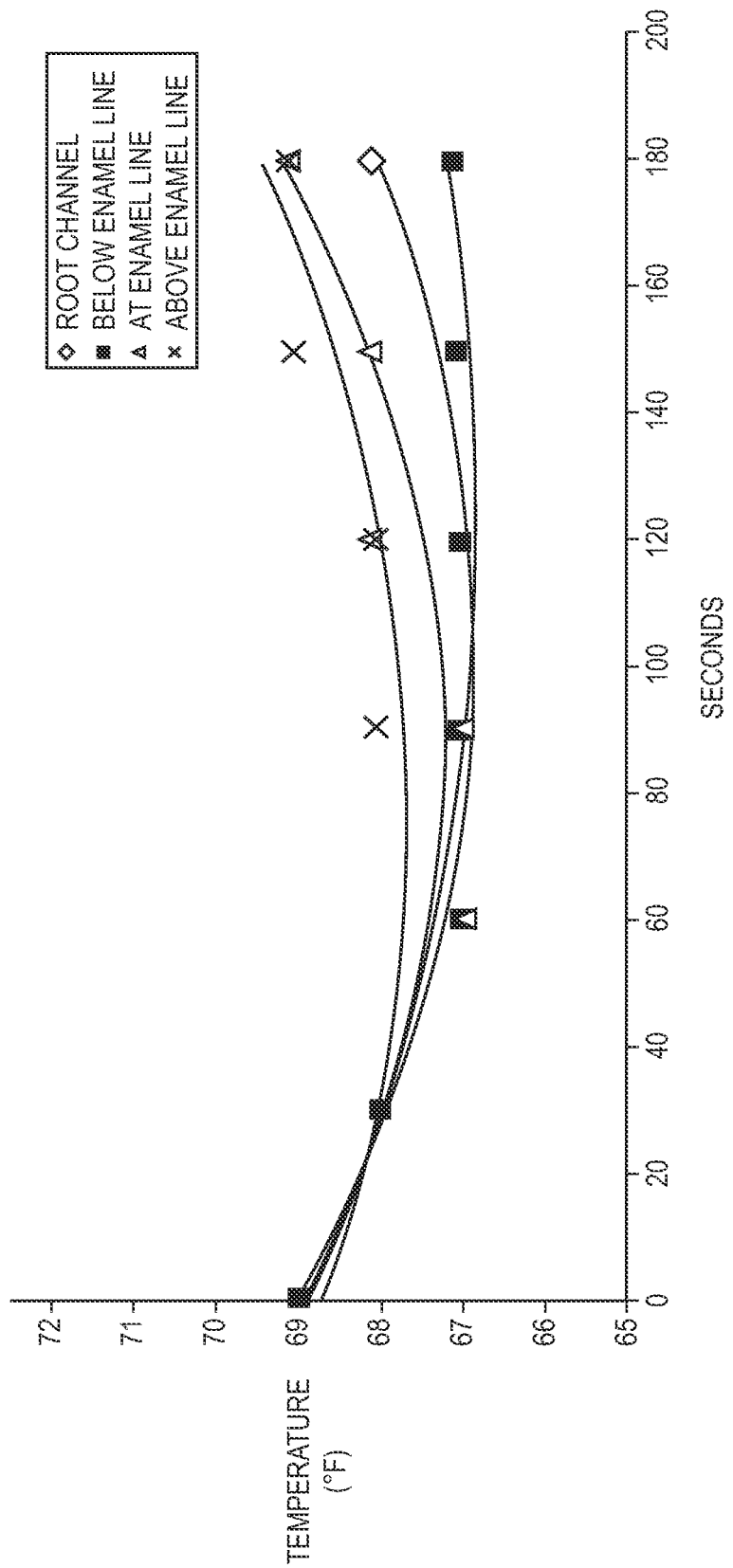
FIG. 8 shows the temperatures observed by various thermocouples during treatment using the experimental system in accordance with the present invention.

The temperature profile of the four molars is shown in FIG. 8. In a thermocouple mounted approximately 2 mm above the nerve chamber, at the beginning of the treatment, the temperature of the molar's nerve chamber dropped due to the convection effect of the water mist on the molar and then rose slightly only reaching substantially the initial temperature. In vivo molars are at higher temperatures and the water mist will have even a more significant cooling effect on these molars. In general, it is desirable that the procedure not increase the temperature of remaining material substantially. For example, a local temperature rise of up to about 5° C. may be suitable, as an upper limit for the pulp temperature rise. Lower temperature rise values are generally preferred, to provide patient comfort (e.g., up to about 1-3° C.).

Figure 9:
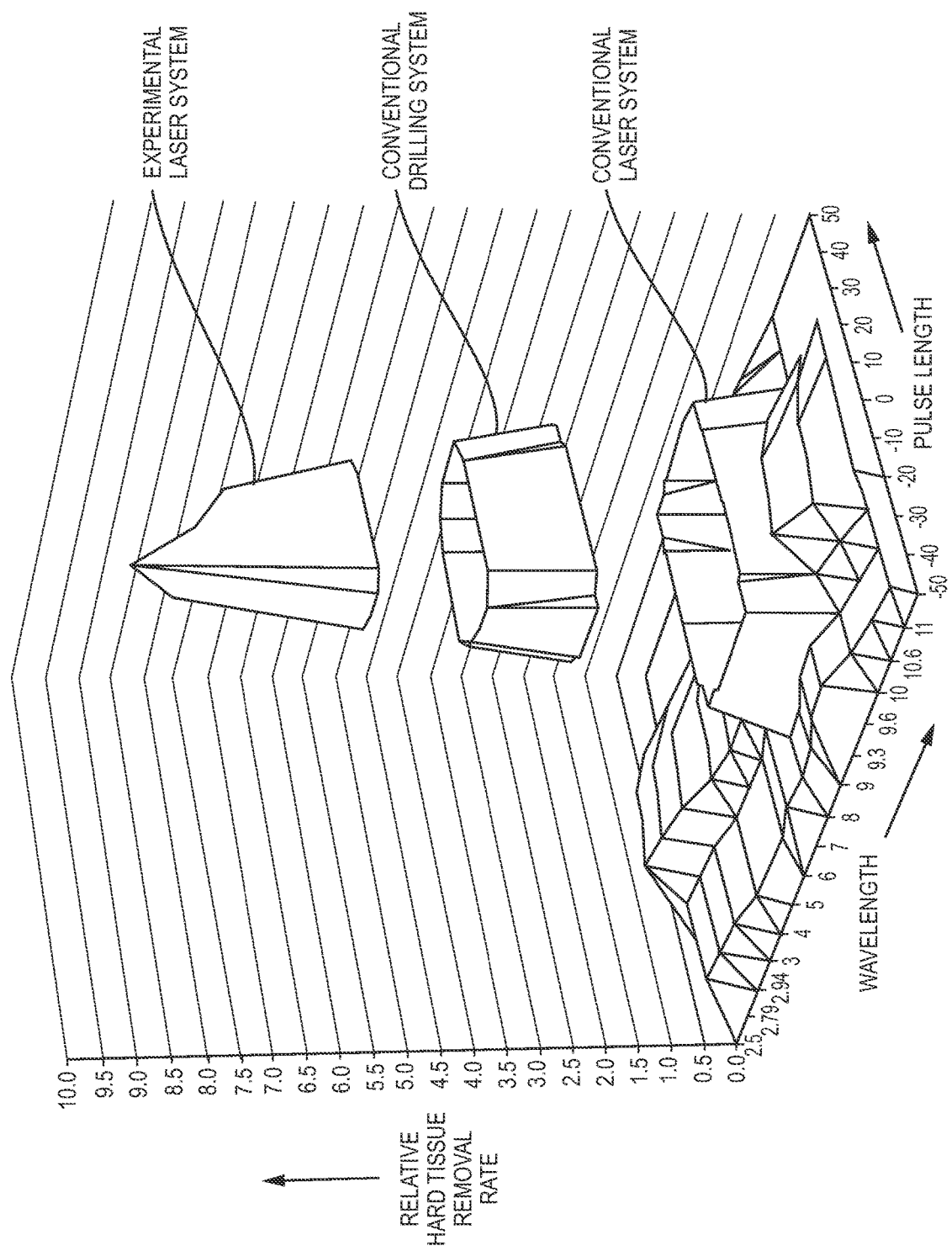
FIG. 9 depicts relative performances of an exemplary laser system according to the present invention, and conventional systems.

The cutting experiments as described above show that the exemplary laser system can cut at least as quickly as a conventional rotating dental hand-piece burr and much more quickly than conventional dental laser systems. The cutting rates corresponding to this exemplary system according to the invention, a conventional burr drilling system, and a conventional dental laser system are shown in FIG. 9.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. For example, it is possible that the described laser and laser system could be used in other (non-dental) applications, such as cutting or contouring bone. It is intended by the following claims to claim that which is literally described and all equivalents thereto, including all modifications and variations that fall within the scope of each claim.

What is claimed is:

1. A method for treating hard dental tissue, the method comprising steps of:
    generating a radio frequency (RF) excited laser beam with a $CO_2$ laser operating with a gas in a range of 260 Torr to 600 Torr, the laser beam having an energy profile, a wavelength in a range of 9 μm to 10 μm, a pulse length of at least 5 μsec, and a repetition rate greater than 0.5 kHz, wherein the laser beam is powered by (i) a direct current (DC) power supply comprising a continuous wave (CW) DC section and a pulsed DC section powering (ii) an RF power supply coupled in series downstream of the DC power supply;
    directing the laser beam at an exposed surface of the hard dental tissue through an optical component, such that the laser beam has a focal region either above or below the exposed surface and, at the exposed surface, has a spot size diameter in a range of 300 μm to 2000 μm;
    controlling at least one of the wavelength, a pulse length, and the repetition rate of the laser beam to produce a pulse energy in a range of 0.1 mJ to 30 mJ; and
    removing by ablation at least a portion of the exposed surface of the hard dental tissue using the pulse energy in a portion either above or below the focal region.

2. The method of claim 1, wherein the laser beam comprises a fluence in a range of up to 50 $J/cm^2$.

3. The method of claim 1, wherein the repetition rate comprises a range of up to 4 kHz.

4. The method of claim 1, wherein the gas is selected from the group consisting of $^{12}C(^{18}O)_2$ gas and $^{12}C(^{16}O)_2$ gas.

5. The method of claim 1, wherein the laser beam is directed at the exposed surface of the hard dental tissue utilizing a hollow waveguide.

6. The method of claim 5, wherein positioning of the hollow waveguide relative to the exposed surface of the hard dental tissue is manually controlled.

7. The method of claim 5, wherein positioning of the hollow waveguide relative to the exposed surface of the hard dental tissue is robotically controlled.

8. The method of claim 1, wherein the laser beam is moved relative to the exposed surface of the hard dental tissue to remove incrementally the portion of the exposed surface of the hard dental tissue.

9. The method of claim 1, wherein a remaining portion of the hard dental tissue does not exhibit charring.

10. The method of claim 1, wherein the hard dental tissue is removed at a rate of up to 0.5 g/sec.

11. The method of claim 1, wherein the hard dental tissue is removed at a volumetric rate of up to 0.17 $cm^3$/sec.

12. The method of claim 1, wherein the hard dental tissue ablation comprises explosive vaporization.

13. The method of claim 1, further comprising the step of directing a fluidic flow at the exposed surface of the hard dental tissue.

14. The method of claim 13, wherein the fluidic flow is selected from the group consisting of a liquid, a gas, and combinations thereof.

15. The method of claim 13, wherein the fluidic flow is adapted to at least one of:
    contribute to controlling temperature of the hard dental tissue; and
    contribute to reducing redeposition of removed material onto the exposed surface of the hard dental tissue.

16. The method of claim 13, wherein the fluidic flow is directed to the exposed surface of the hard dental tissue at an angle of incidence in a range from 65 degrees to 90 degrees.

17. The method of claim 1, wherein the hard dental tissue is selected from the group consisting of dental enamel, dentin, and bone.

18. The method of claim 1, wherein during a single pulse the laser beam is adapted to contact a cross-sectional area in a range of 0.07 $mm^2$ to 3.14 $mm^2$ of the exposed tissue.

19. The method of claim 1, wherein the step of directing the laser beam comprises delivering sequences of pulses for up to three minutes.

20. The method of claim 1, wherein the laser beam is directed to the exposed surface of the hard dental tissue at an angle of incidence up to 90 degrees.

21. The method of claim 1, wherein the step of directing the laser beam comprises:
    focusing the laser beam using a lens having a focal length different from a distance of the exposed surface of the hard dental tissue relative to the lens.

22. The method of claim 1, wherein the step of directing the laser beam comprises modifying the laser beam using an optical system, such that an energy profile of the modified laser beam is non Gaussian.

* * * * *